United States Patent [19]

Nappa et al.

[11] Patent Number: 6,066,769
[45] Date of Patent: May 23, 2000

[54] PROCESS FOR THE MANUFACTURE OF HALOGENATED PROPANES CONTAINING END-CARBON FLUORINE

[75] Inventors: Mario Joseph Nappa, Newark, Del.; Allen Capron Sievert, Elkton, Md.; Edwin J. Warwas, Wilmington, Del.

[73] Assignee: E. I. du Pont de Nemours and Company, Wilmington, Del.

[21] Appl. No.: 09/155,841

[22] PCT Filed: Apr. 4, 1997

[86] PCT No.: PCT/US97/06013

§ 371 Date: Oct. 6, 1998

§ 102(e) Date: Oct. 6, 1998

[87] PCT Pub. No.: WO97/37956

PCT Pub. Date: Oct. 16, 1997

Related U.S. Application Data

[60] Provisional application No. 60/015,270, Apr. 10, 1996.

[51] Int. Cl.$^7$ .................................................. C07C 17/08
[52] U.S. Cl. ...................... 570/169; 570/166; 570/167; 570/168
[58] Field of Search ..................................... 570/167, 169, 570/168, 166

[56] References Cited

U.S. PATENT DOCUMENTS

| | | | |
|---|---|---|---|
| 3,381,044 | 4/1968 | Wiedemann et al. | 260/653.7 |
| 5,414,165 | 5/1995 | Nappa et al. | 570/169 |
| 5,616,819 | 4/1997 | Boyce et al. | 570/167 |

FOREIGN PATENT DOCUMENTS

| | | |
|---|---|---|
| 2073533 | 7/1992 | Canada . |
| 0 522 639 | 1/1993 | European Pat. Off. . |
| WO 97/08117 | 3/1997 | WIPO . |

*Primary Examiner*—Alan Siegel

[57] ABSTRACT

A process is disclosed for producing a compound of the formula: $CF_3CHXCF_{3-z}Y_z$ where X and Y are independently selected from the group consisting of H and Cl, and z is 0 or 1. The process involves (1) contacting $CCl_3CHXCC_{3-z}Y_z$, $CCl_{2-z}=CXCC_3$, and/or $CCl_2CX=CC_{3-z}Y_z$ starting material, with hydrogen fluoride at a temperature of less than 200° C. to produce a fluorination product of said starting material which includes at least 90 mole percent total of $C_3HXY_zCl_{6-z-x}F_x$ saturated compounds and $C_3XY_zCl_{5-z-y}F_y$ olefinic compounds, wherein x is an integer from 1 to 6-z and y is an integer from 1 to 5-z, (the fluorination product including no more than about 40 mole percent of the desired product, $CF_3CHXCF_{3-z}Y_z$); (2) contacting saturated compounds and olefinic compounds produced in (1) with hydrogen fluoride in the vapor phase at a temperature of from 200° C. to about 400° C. in the presence of a fluorination catalyst; and (3) reacting a sufficient amount of said compounds, wherein x is an integer from 1 to 5-z and olefinic compounds produced in (1) with hydrogen fluoride in the vapor phase at a temperature of from 200° C. to about 400° C. in the presence of a vapor phase fluorination catalyst to provide an overall selectivity to $CF_3CHXCF_{3-z}Y_z$ of at least about 90 percent based upon the amount of starting material reacted with HF in (1) and (2).

11 Claims, No Drawings

PROCESS FOR THE MANUFACTURE OF HALOGENATED PROPANES CONTAINING END-CARBON FLUORINE

This application is a national filing under 35 USC 371 of International Application No. PCT/US97/06013 filed Apr. 4, 1997 and claims priority of U.S. Provisional Application Ser. No. 60/015,270 filed Apr. 10, 1996.

FIELD OF THE INVENTION

This invention relates to a process for the manufacture of halogenated propanes containing at least five fluorine substituents, and more particularly to the manufacture of halogenated propanes containing at least five end-carbon fluorine substituents (e.g., $CF_3CH_2CF_3$) by the reaction of selected saturated compounds (e.g., $CCl_3CH_2CCl_3$) and/or unsaturated compounds (e.g., $CCl_2=CHCCl_3$) with hydrogen fluoride.

BACKGROUND

Compounds such as 1,1,1,3,3,3-hexafluoropropane (i.e., HFC-236fa) have found uses as refrigerants, fire extinguishants, heat transfer media, gaseous dielectrics, sterilant carries, polymerization media, particulate removal fluids, carrier fluids, buffing abrasive agents, displacement drying agents and power cycle working fluids. More particularly, HFC-236fa itself is a highly effective and environmentally acceptable fire extinguishant and refrigerant.

Canadian Patent No. 2,073,533 discloses a liquid phase process for the manufacture of HFC-236fa by contacting HCC-230fa with HF in the presence of a liquid phase catalyst (e.g., tin and antimony compounds). All of the 1,1,1,3,3,3-hexachloropropane is converted to 1-chloro-1,1,3,3,3-pentafluoropropane (i.e., HCFC-235fa) and HFC-236fa with a selectivity of greater than 45 mole % with respect to HFC-236fa. The separation of pure HFC-236fa is complicated by the presence of HCFC-235fa. Moreover, vapor processes are often preferred because operational advantages (e.g., HF corrosivity problems ware typically exacerbated in the liquid phase).

U.S. Pat. No. 5,414,165 discloses a vapor phase process for the manufacture of HFC-236fa by contacting HCC-230fa (and sufficient haloprecursors of HFC-236fa) with HF in the presence of a trivalent chromium catalyst.

$CCl_3CH_2CCl_3$ (HCC-230fa) is a high boiling liquid (b.p. 206° C. at 101.3 kPa). Efficient use of a catalytic vapor phase reactor requires that HCC-230fa be fed to the reactor as a vapor. Feeding liquid directly to a catalyst bed is well known in the art to cause deactivation of the catalyst. Evaporation of HCC-230fa in a vaporizer of standard design can cause substantial degradation to HCl, $CCl_3CH=CCl_2$, and in particular, undesirable higher boiling materials such as chlorinated six-carbon compounds and tars. Furthermore, the fluorine-chlorine exchange reaction is typically highly exothermic. Replacing all six chlorines of HCC-230fa with fluorine to produce HFC-236fa in the catalytic reactor can cause heat management problems.

SUMMARY OF THE INVENTION

A process is provided in accordance with this invention for producing a compound of the formula $CF_3CHXCF_{3-z}Y_z$ where X and Y are independently selected from the group consisting of H and Cl, and z is 0 or 1. The process comprises (1) contacting starting material selected from the group consisting of a compound of the formula $CCl_3CHXCCl_{3-z}Y_z$, a compound of the formula $CCl_2=CXCCl_{3-z}Y_z$, a compound of the formula $CCl_2=CXCCl_{3-z}Y_z$ and mixtures thereof, with hydrogen fluoride at a temperature of less than 200° C. to produce a fluorination product of said starting material which includes at least 90 mole percent of compounds selected from the group consisting of saturated compounds having the formula $C_3HXY_zCl_{6-z-x}F_x$ and olefinic compounds of the formula $C_3XY_zCl_{5-z-y}F_y$, wherein x is an integer from 1 to 6-z and y is an integer from 1 to 5-z, said fluorination product including no more than about 40 mole percent $CF_3CHXCF_{3-z}Y_z$; (2) contacting compounds selected from the group consisting of said saturated compounds and said olefinic compounds produced in (1) with hydrogen fluoride in the vapor phase at a temperature of from 200° C. to about 400° C. in the presence of a fluorination catalyst; and (3) reacting a sufficient amount of said saturated compounds, wherein x is an integer from 1 to 5-z and said olefinic compounds produced in (1) with hydrogen fluoride in the vapor phase at a temperature of from 200° C. to about 400° C. in the presence of a vapor phase fluorination catalyst to provide an overall selectivity to $CF_3CHXCF_{3-z}Y_z$ of at least about 90 percent based upon the amount of starting material reacted with HF in (1) and (2).

DETAILED DESCRIPTION

The process of this invention is particularly noted for producing $CF_3CH_2CF_3$ (i.e., a compound where X is H and z is 0) from $CCl_3CH_2CCl_3$ (i.e., HCC-230fa) starting material. Problems associated with vapor phase reaction of HCC-230fa at relatively high temperature can be reduced by pre-fluorinating the HCC-230fa in a first step and completing the fluorination in a second, vapor phase step. In addition, pre-fluorinating HCC-230fa to a mixture of fluorinated alkanes and alkenes gives a product that is thermally more stable than the pure HCC-230fa with respect to tar formation. Also, the mixture of fluorinated alkanes and alkenes resulting from pre-fluorinating HCC-230fa can be vaporized at lower temperature than HCC-230fa itself, which translates to fewer fouling problems in the vaporizer.

Accordingly, the process of this invention provides a multi-step method for manufacture of $CF_3CH_2CF_3$ (HFC-236fa) from $CCl_3CH_2CCl_3$ (HCC-230fa): In the first step of the process, HCC-230fa is contacted with hydrogen fluoride (HF) to form a mixture of fluorinated compounds. The hydrogen fluoride used should be anhydrous. The contacting of HCC-230fa and HF may be conducted in the liquid phase in one of several ways. The process of the invention may be conducted in batch, semi-continuous, or continuous modes. In the batch mode, liquid HCC-230fa and hydrogen fluoride are typically combined in an autoclave or other suitable reaction vessel and heated to the desired temperature. Preferably, the process of the invention is carried out by feeding liquid HCC-230fa to a reactor containing HF, or a mixture of HF and fluorinated compounds formed by reacting HF with HCC-230fa, held at the desired reaction temperature. Alternatively, HF may be fed to a reactor containing HCC-230fa, or a mixture of HCC-230fa and a mixture of fluorinated compounds formed by reacting HF with HCC-230fa.

In another embodiment, both HF and HCC-230fa may be fed concurrently in the desired stoichiometric ratio to a reactor containing a mixture of HF and fluorinated compounds formed by reacting HF with HCC-230fa.

In yet another embodiment, liquid HCC-230fa and HF may be fed to a heated tubular reactor. The reactor may be empty, but is preferably filled with a suitable packing such as Monel® nickel alloy turnings or wool, Hastelloy® nickel alloy turnings or wool, or other material which allows efficient mixing of liquid HCC-230fa with hydrogen fluoride vapor. Said tubular reactor is preferably oriented vertically with HCC-230fa liquid entering the top of the reactor and pre-heated HF vapor introduced at the bottom of the reactor. The HCC-230fa feed rate is determined by the length and diameter of the reactor, the temperature, and the degree of fluorination desired. Slower feed rates at a given temperature will increase contact time and tend to increase the amount of conversion of starting material and the amount of fluorine in the products.

In a further embodiment, the reactor effluent from the first reaction zone, where HCC-230fa is reacted with HF, is fed to a second reactor zone where HFC-236fa with an overall selectivity of at least 90% based on the amount of HCC-230fa reacted with HF is produced. Saturated compounds of the formula $C_3H_2Cl_{6-x}F_x$ and/or olefinic compounds of the formula $C_3HCl_{5-y}F_y$ where x is an integer from 1 to 6 and y is an integer from 1 to 5 possibly as well as some unreacted HCC-230fa (another saturated compound) and/or $CCl_3CH=CCl_2$ (another olefinic compound) are also present in the second reaction zone. After separation of HFC-236fa, these saturated and olefinic compounds in the effluent from the second reaction zone may be recycled to the first reaction zone or to the second reaction zone, or to both the first and second reaction zones.

Temperatures suitable for reacting HCC-230fa with HF in step (1) are from about 80° C. to about 200° C., preferably from about 100° C. to about 180° C., most preferably from about 120° C. to about 175° C. Higher temperatures result in higher conversions of HCC-230fa and a greater degree of fluorination. The degree of fluorination reflects the number of fluorine substituents that replace chlorine substituents in the HCC-230fa starting material. For example, the products 1,1-dichloro-3,3,3-trifluoro-1-propene or 1,1,1-trichloro-3,3,3-trifluoropropane represent a higher degree of fluorination than the products 1,1,3-trichloro-3,3-difluoro-1-propene or 1,1,1,3-tetrachloro-3,3-difluoropropane.

The pressure of step (1) is not critical and in batch reactions is usually taken to be the autogenous pressure of the system at the reaction temperature. The pressure of the system increases as hydrogen chloride is formed by replacement of chlorine substituents for fluorine substituents in the HCC-230fa starting material. In a continuous process it is possible to set the pressure of the reactor in such a way that the HCl liberated by the reaction is vented from the reactor. Typical reaction pressures are from about 20 psig (239 kPa) to about 1000 psig (6994 kPa).

The molar ratio of HF to HCC-230fa employed in step (1) is typically from about 1:1 to about 100:1 and is preferably from about 1:1 to about 20:1, more preferably from about 3:1 to about 8:1.

Fluorinated saturated and olefinic compounds formed by contacting HCC-230fa with HF in step (1) can include, for example, 1-chloro-1,3,3,3-tetrafluoro-1-propene (HCFC-1224zb), 1,1-dichloro-1,3,3,3-tetrafluoropropane (HCFC-234fb), 1,3-dichloro-1,1,3,3-tetrafluoropropane (HCFC-234fa), 1,1-dichloro-3,3,3-trifluoro-1-propene (HCFC-1223za), 1,1,1-trichloro-3,3,3-trifluoropropane (HCFC-233fb), 1,1,3-trichloro-1,3,3-trifluoropropane (HCFC-233fa), 1,1,3-trichloro-3,3-difluoro-1-propene (HCFC-1222za), 3,3,3-trichloro-1,1-difluoro-1-propene (HCFC-1222zc), 1,1,1,3-tetrachloro-3,3-difluoropropane (HCFC-232fb), 1,1,3,3-tetrachloro-1,3-difluoropropane (HCFC-232fa), 1,1,3,3-tetrachloro-3-fluoro-1-propene (HCFC-1221za), 1,3,3,3-tetrachloro-1-fluoro-1-propene (HCFC-1221zb) and 1,1,1,3,3-pentachloro-3-fluoropropane (HCFC-231fa). In addition, small amounts of 1-chloro-1,1,3,3,3-pentafluoropropane (HCFC-235fa), and 1,1,3,3,3-pentafluoro-1-propene (HFC-1225zc) may also be formed, particularly if a catalyst is present. When $CCl_3CH_2CCl_3$ is used as the starting material, small amounts of $CCl_3CH=CCl_2$ (another possible starting material) can be formed in addition to fluorinated compounds. The step (1) reaction is controlled to provide a fluorinated product which includes no more than about 40 mole percent HFC-236fa.

Of note are 1,1,3,3-tetrachloro-1,3-difluoropropane (i.e., $CCl_2FCH_2CCl_2F$ or HCFC-232fa), 1,1,3,3-tetrachloro-3-fluoro-1-propene (i.e., $CCl_2=CHCCl_2F$ or HCFC-1221za), 1,3,3,3-tetrachloro-1-fluoro-1-propene (i.e., $CClF=CHCCl_3$ or HCFC 1221zb) and 1,1,1,3,3-pentachloro-3-fluoropropane (i.e., $CCl_3CH_2CCl_2F$ or HCFC-231fa) which are considered novel compounds.

The saturated compounds $C_3H_2Cl_{6-x}F_x$ (x is 1 to 6) and olefinic compounds $C_3HCl_{5-y}F_y$ (y is 1 to 5) formed by contacting HCC-230fa with HF constitute at least 90 mole % of the reaction product, preferably at least 95 mole % of the reaction product and more preferably at least 99 mole % of the reaction product of step (1).

A catalyst is not needed for the first step of the fluorination of HCC-230fa, but may be added if desired to increase the conversion of HCC-230fa, the rate of the reaction, or the degree of fluorination of the fluorinated compounds produced. Suitable liquid phase fluorination catalysts which may be used in the first step of the fluorination (when carried out in the liquid phase) include carbon, $AlF_3$, $BF_3$, $FeZ_3$ where Z is selected from the group consisting of Cl and F, $FeZ_3$ supported on carbon, $SbCl_{3-a}F_a$ (a=0 to 3), $AsF_3$, $MCl_{5-b}F_b$ (M=Sb, Nb, Ta, Mo; b=0 to 5), and $M'Cl_{4-c}F_c$ (M'=Sn, Ti, Zr, Hf; c=0 to 4).

The fluorinated compounds produced by contacting HCC-230fa with HF may be used directly in the next step of the process or may be subjected to one of several purification schemes. Preferably, the reaction is carried out in such a way that the HCl produced during the fluorination of HCC-230fa is removed via a distillation column present in the system. The same or a different distillation column may remove reaction products having the desired degree of fluorination from the reactor, leaving unconverted HCC-230fa or products having a lower degree of fluorination in the reactor for further reaction. The fluorinated products removed from the reactor are then sent to a vaporizer or heated zone where they are brought to the desired temperature of the second step of the fluorination process. Alternatively, the entire reaction effluent formed by contacting HCC-230fa with HF in the first reaction zone may be sent to a vaporizer or heated zone and then to the second step of the fluorination process optionally with the further addition of HF. Of note are embodiments wherein the conversion of $CCl_3CH_2CCl_3$ in (1) is at least about 60%; and wherein the mole ratio of $CCl_3CH_2CCl_3$ which is contacted with HF in (2) to the total of the saturated compounds and the olefinic compounds produced in (1) which are contacted with HF in (2) is less than about 2:3.

In the process for producing HFC-236fa from HCC-230fa, products produced in the first step (i.e., compounds selected from the group consisting of saturated compounds of the formula $C_3H_2Cl_{6-x}F_x$ and olefinic compounds of the formula $C_3HCl_{5-y}F_y$ wherein x is an integer from 1 to 5 and y is an integer from 1 to 5) are subsequently reacted (together with unreacted $CCl_3CH_2CCl_3$ and any $CCl_3CH=CCl_2$, as desired) with HF and in the presence of vapor phase catalysts. Preferably a sufficient amount of these compounds produced in the first step are reacted to provide an overall selectivity to $CF_3CH_2CF_3$ of at least about 95 percent based upon the amount of $CCl_3CH_2CCl_3$ reacted with HF.

Vapor phase fluorination catalysts which may be used include metals (including elemental metals, metal oxides and/or other metal salts); alumina; fluorided alumina; aluminum fluoride; metals on alumina; metals on aluminum fluoride; magnesium fluoride on aluminum fluoride; metals on fluorided alumina; alumina on carbon; aluminum fluoride on carbon; fluorided alumina on carbon; metals on carbon; chromium catalysts (e.g., $Cr_2O_3$ by itself or with other metals such as Mg and/or Zn); mixtures of metals, aluminum fluoride, and graphite; and chromium-magnesium optionally on graphite.

Suitable metals for use as catalysts (optionally on alumina, aluminum fluoride, fluorided alumina or carbon) include chromium, Group VIII metals (iron, cobalt, nickel, ruthenium, rhodium, palladium, osmium, iridium, platinum), Group VIIB metals (manganese, rhenium), Group IIIB metals (scandium, yttrium, lanthanum), Group IB metals (cooper, silver, gold), zinc and/or metals having an atomic number of 58 through 71 (cerium, praseodymium, neodymium, promethium, samarium, europium, gadolinium, terbium, dysprosium, holmium, erbium, thulium, ytterbium or lutetium). Preferably, when used with a support, the total metal content of the catalyst will be from about 0.1 to 20 percent by weight; typically, from about 0.1 to 10 percent by weight.

Fluorided alumina and aluminum fluoride can be prepared as described in U.S. Pat. No. 4,902,838. Metals on aluminum fluoride and metals on fluorided alumina can be prepared by procedures described in U.S. Pat. No. 4,766,260. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in Canadian Pat. No. 2,025,145. Other metals and magnesium optionally on graphite can be prepared in a similar manner to the latter patent.

Preferred vapor phase fluorination catalysts (especially where selectivity to HFC-236fa of about 95 percent or more is desired based on the amount of $CCl_3CH_2CCl_3$ reacted with HF) include catalysts comprising trivalent chromium. Of particular note is $Cr_2O_3$ prepared by pyrolysis of $(NH_4)_2Cr_2O_7$, $Cr_2O_3$ having a surface area greater than about 200 $m^2/g$, and $Cr_2O_3$ prepared by pyrolysis of $(NH_4)_2Cr_2O_7$ or having a surface area greater than about 200 $m^2/g$ which is pretreated with a vaporizable fluorine-containing compound (e.g., HF or $CCl_3F$). These pretreated catalysts are most preferred, and are suitable for obtaining at least about 90% selectivity to HFC-236fa.

The $Cr_2O_3$ catalyst prepared by the pyrolysis of ammonium dichromate suitable for the process of this invention can be prepared by any method known to the art including those disclosed in U.S. Pat. Nos. 4,843,181 and 5,036,036, which are hereby incorporated herein by reference. The $Cr_2O_3$ obtained by such pyrolysis may contain low levels of contaminants which are present as a result of the manufacturing process for the original $(NH_4)_2Cr_2O_7$. Although not totally destructive of catalyst efficacy, potassium, for example, as a contaminant has an adverse effect on the activity and life of the catalyst of this invention. It is desirable for the amount of potassium and other alkali metals to be 100 ppm by weight or less. The level may be reduced by a water-washing step. While the conditions are not critical, the water-washing step can include forming a slurry containing 5–15% $Cr_2O_3$, preferably 10%, and deionized water. Stirring of this water slurry can be carried out at 35–65° C. for at least one hour, preferably two or more hours. The solids are then recovered by filtration, suitably on a plate and frame filter press. The filter cake can be analyzed for alkali metal content. If its level is 100 ppm by weight or less (dry basis), the solids are, thereafter, dried. If not, the washing step can be repeated to obtain a desired level of alkali metal content.

Other $Cr_2O_3$ catalysts which may be used in the process of this invention include catalysts having a surface area greater than about 200 $m^2/g$, some of which are commercially available.

The form of the catalyst is not critical and may be used as pellets, powders or granules.

Generally, the resulting $Cr_2O_3$ will be pretreated with Hf. It is thought that this converts some of the surface chrome oxide to chrome oxyfluoride. This pretreatment can be accomplished by placing the $Cr_2O_3$ in a suitable container, which can be the reactor to be used to perform the second reaction step of the instant invention, and thereafter, passing HF over the pyrolyzed and dried $Cr_2O_3$ so as to partially saturate the $Cr_2O_3$ with HF. This is conveniently carried out by passing HF over the $Cr_2O_3$ for a period of time, for example, about 15 to 300 minutes at a temperature of, for example, about 200° C. to about 450° C. The purpose of this pretreatment is to prevent damage to the catalyst due to possible high temperature excursions and resultant coking of the catalyst if the organic reactants were contacted with the catalyst without first having conditions some of the surface chrome oxide with HF. Nevertheless, this pretreatment is not essential; initial process conditions and equipment could be selected so as to avoid the problem of high temperature and coking of the catalyst.

The process aspects may be combined in various ways. For example, in step (1), $CCl_3CH_2CCl_3$ may be reacted with HF in the liquid phase in a first reaction zone; compounds selected from the group consisting of saturated compounds having the formula $C_3H_2F_xCl_{6-x}$ and olefinic compounds having the formula $C_3HF_yCl_{5-y}$ may be vaporized from said first reaction zone at a temperature less than 200° C. and fed to a second reaction zone; and the contact of (2) may then be in said second reaction zone. Also of note are embodiments wherein step (1) is carried out in a first reaction zone and (2) is carried out in a second reaction zone, and wherein essentially the entire effluent from the first reaction zone is fed to the second reaction zone; and embodiments wherein step (1) is carried out in a first reaction zone and (2) is carried out in a second reaction zone, and wherein compounds selected from the group consisting of saturated compounds of the formula $C_3H_2F_xCl_{6-x}$ and olefinic compounds of the formula $C_3HF_yCl_{5-y}$ are recycled from the second reaction zone to the first reaction zone, or to the second reaction zone or to both the first and second reaction zones.

While the detailed description above has focused on the production of HFC-236fa from HCC-230fa, other starting materials and products may also be used. For example, hexachloropropene ($CCl_2=CClCCl_3$) may be used as a starting material to produce HCFC-226da ($CF_3CHClCF_3$) or HCFC-225da (CF$_3$CHClCClF$_2$), 1,1,1,3,3-pentachloropropene (CCl$_3$CH=CCl$_2$) may be used as a starting material to produce HFC-236fa (CF$_3$CH$_2$CF$_3$) or HCFC-235fa (CF$_3$CH$_2$CClF$_2$), and 1,1,1,3,3-pentachloropropane (HCC-240fa) may be used as a starting material to produce 1,1,1,3,3-pentafluoropropane (HFC-245fa). The fluorinated compounds produced by contacting HF with hexachloropropene or HCC-240fa, etc., can of course be different than those produced by reacting HF with HCC-230fa. HCFC-226da is a valuable intermediate for HFC-236fa, HCFC-235fa is an intermediate for producing CF$_3$CH=CHF (a polymerization feed material), HCFC-225da is useful as a cleaning solvent and HFC-245fa is an alternative to CFC-11 as a blowing agent.

The reaction zone and its associated feed lines, effluent lines and associated units should be constructed of materials resistant to hydrogen fluoride.

Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

| Legend | |
|---|---|
| HFC-236fa | CF$_3$CH$_2$CF$_3$ |
| HCFC-235fa | CF$_3$CH$_2$CClF$_2$ |
| HCFC-234fb | CF$_3$CH$_2$CCl$_2$F |
| HCFC-1223za | CF$_3$CH=CCl$_2$ |
| HCC-230fa | CCl$_3$CH$_2$CCl$_3$ |

EXAMPLE 1

Reaction of 1,1,1,3,3,3-Hexachloropropane with HF in the Absence of Catalyst

A 160 mL Hastelloy® C nickel alloy Parr reactor equipped with a magnetically driven agitator, pressure transducer, vapor phase sampling valve, thermal well, and valve was charged with 50 g (2.5 moles) of HF via vacuum transfer. The autoclave was brought to 0° C. and charged with 10.3 g (0.041 mole) of HCC-230fa via a cylinder pressurized with nitrogen. The pressure at 14° C. was 56 psig (487 kPa).

The autoclave was then set to heat to 120° C. Within 15 minutes the temperature reached 133° C. at 333 psig (2397 kPa). The temperature subsided to 120° C. within about 7 minutes; the pressure at 120° C. climbed from about 327 psig (2355 kPa) to 382 psig (2734 kPa) over the course of about 1.8 h.

A sample of the reactor vapor at this point had the following composition:

| Component | GC Area % |
|---|---|
| 236fa | 0.9 |
| 235fa | 1.6 |
| 234fb | 24.4 |
| 1223za | 69.6 |
| Unknowns | 2.0 |

COMPARATIVE EXAMPLE A

Reaction of 1,1,1,3,3,3-hexachloropropane with HF in the Presence Zirconium Tetrachloride A 160 mL Hastelloy® C nickel alloy Parr autoclave equipped with a magnetically driven agitator, pressure transducer, vapor phase sampling valve, thermal well, and valve was charged with 9.1 g (0.039 mmole) of ZrCl$_4$. The reactor was sealed and 50 g (2.5 moles) of HF introduced to the reactor via vacuum transfer. The autoclave was brought to 8° C. and stirred for 15 minutes; the pressure rose to 103 psig (811 kPa) at a final temperature of 15° C. The autoclave was vented to 0 psig (101 kPa) and then charged with 10.1 g (0.040 mole) of HCC-230fa via a cylinder pressurized with nitrogen.

The autoclave was then set to heat to 120° C. Within 17 minutes the temperature reached 120° C. and the pressure reached 272 psig (1976 kPa). The temperature was held at 120° C. for 2 h; the pressure climbed to 440 psig (3134 kPa).

A sample of the reactor vapor at this point had the following composition:

| Component | GC Area % |
|---|---|
| 236fa | 0.2 |
| 235fa | 3.5 |
| 234fb | 73.4 |
| 1223za | 21.7 |

Comparison of these results with those of Example 1 show the similarity of both the catalyzed and uncatalyzed HF exchange reaction with CCl$_3$CH$_2$CCl$_3$. The major difference is the amounts of 1223za (CF$_3$CH=CCl$_2$) and 234fb (CF$_3$CH$_2$CCl$_2$F) which are reversed in the two runs. CF$_3$CH=CCl$_2$ is readily converted to CF$_3$CH$_2$CCl$_2$F by HF addition.

EXAMPLE 2

Reaction of 1,1,1,3,3,3-Hexachloropropane with HF in a Prereactor in Absence of Added Catalyst Followed by Reaction of the Prereactor Effluent over a Chrome Oxide Catalyst in the Vapor Phase Liquid HCC-230fa was fed directly in to the center of a ¼" 6.4 mm) stainless steel Swagelok® cross using ¹⁄₁₆" (1.6 mm) stainless steel tubing through one of the horizontal ports. The other horizontal port is unused in this experiment. Four ¼" (6.4 mm) Monel® nickel alloy discs are pressed into the bottom port of the cross to act as inert surface for reaction of the HCC-230fa and HF. HF vapor was passed up through the bottom port and the Monel® nickel alloy discs where reaction occurs with the liquid HCC-230fa. The reaction products were then passed through the upper port of the cross and through ¼" (6.4 mm) heated stainless steel tubing (approximately 36 inches, (914 mm)) into a vapor phase reactor, which was a 15 in. (381 mm)×½ in. (1.3 mm) Inconel® 600 alloy tube and was filled with 17.12 g (about 13 mL) of a chromium oxide catalyst, prepared by the pyrolysis of ammonium dichromate, ground to 12/20 mesh (1.68/0.84 mm).

HCC-230fa (1.09 mL/hour, 2.9 sccm, $4.8 \times 10^{-8}$ m$^3$/s) and anhydrous HF (27.4 sccm, $4.6 \times 10^{-7}$ m$^3$/s) were fed for 315 hours with no sign of vapor phase catalyst deactivation. Below is a summary of different conditions (each condition is an average of six contiguous gas chromatographic analyses taken one hour apart):

| Prereactor T °C. | VP[2] T °C. | Yield HFC-236fa |
|---|---|---|
| 127 | 275 | 89% |
| 153 | 275 | 96% |
| 178 | 275 | 99% |
| 178 | 250 | 83% |
| 178 | 226 | 93% |

[1]VP is the vapor phase reactor temperature

The yield of HFC-236fa is the yield calculated as the moles of HFC-236a in the reactor effluent/moles of HCC-230fa in the feed.

EXAMPLE 3

Reaction of the Product of the Uncatalyzed Liquid Phase Reaction of Hf with 1,1,1,3,3,3-hexachloropropane Catalyst With HF over a Chrome Oxide Catalyst in the Vapor Phase Catalyst Activation A 15 in (381 mm)×⅜ in (9.5 mm) Hastelloy® nickel alloy tube was filled with 2.29 grams (2 mL) of Cr$_2$O$_3$ (12–20 mesh, 1.4-0.83 mm). The catalyst was activated by heating at 200° C. for 17 hours under a nitrogen purge (50 sccm, $8.3 \times 10^{-7}$ m$^3$/s). A flow of HF (50 sccm, $8.3 \times 10^{-7}$ m$^3$/s) was maintained for 15 minutes. The flow of nitrogen was reduced (20 sccm, $3.3 \times 10^{-7}$ m$^3$/s) and the flow of HF was increased (80 sccm, $1.3 \times 10^{-6}$ m$^3$/s) for 40 minutes. The temperature was raised in stages, 250° C. for one hour, 300° C. for 65 minutes, 350° C. for 85 minutes, and to 400° C. for 95 minutes. The temperature was then lowered to 200° C. and maintained for 85 minutes.

Error!

A liquid measure obtained from the reaction of CCl$_3$CH$_2$CCl$_3$ with HF at 175° C. in the liquid phase in the absence of catalyst and consisting essentially of CCl$_2$FCH$_2$CF$_3$, CCl$_2$=CHCF$_3$, CCl$_3$CH$_2$CF$_3$, CCl$_3$CH$_2$CClF$_2$ was passed through the above catalytic reactor at 274° C., at a flow rate of 3.9 sccm ($6.5 \times 10^{-8}$ m$^3$/s, 1.16 mL/hr). HF at a flow rate of 37.3 sccm ($6.2 \times 10^{-7}$ m$^3$/s) was simultaneously passed the above catalytic reactor. The gaseous effluent was analyzed by GC/MS and found to be >99 relative area % CF$_3$CH$_2$CF$_3$. At these flow rates, CF$_3$CH$_2$CF$_3$ was the only organic observed from 224–274° C.

EXAMPLE 4

2% Co/Alumina Fluorination Catalyst

The catalyst was prepared as described in U.S. Pat. No. 4,766,260. The procedure used for activating the catalyst (1.18 g 2 mL) and reacting the CCl$_3$CH$_2$CCl$_3$ fluorination product was the same as that used for Example 3. The results are shown in the table where CT is the contact time in seconds and the percentages were obtained by GC/MS and are in area %.

| T °C. | % 236fa | % 235fa | % 234fb/1223za | CT |
|---|---|---|---|---|
| 240 | 65.2 | 14.2 | 18.7 | 2.8 |
| 275 | 91.3 | 3.0 | 2.7 | 2.8 |

EXAMPLE 5

2% Zn/alumina Fluorination Catalyst

The catalyst was prepared as described in U.S. Pat. No. 5,300,711. The procedure used for activating the catalyst and reacting the CCl$_3$CH$_2$CCl$_3$ fluorination product was the same as that used for Example 3. The results are shown in the table where CT is the contact time in seconds and the percentages were obtained by GC/MS and are in area %.

| T °C. | % 236fa | % 235fa | % 234fb/1223za | CT |
|---|---|---|---|---|
| 242 | 67.5 | 9.7 | 22.2 | 2.8 |
| 276 | 90.4 | 2.8 | 5.6 | 2.8 |

EXAMPLE 6

Reaction of 1,1,1,3,3-Pentachloropropane with HF in the Absence of Catalyst

A 160 mL Hastelloy® C nickel alloy Parr reactor equipped with a magnetically driven agitator, pressure transducer, vapor phase sampling valve, thermal well, and valve was charged with 50 g (2.5 moles) of HF via vacuum transfer. The autoclave was brought to 0° C. and charged with 9.9 g (0.046 mole) of 1,1,1,3,3-pentachloropropane (CCl$_3$CH$_2$CHCl$_2$ or HCC-240fa) via a cylinder pressurized with nitrogen. The pressure at 17° C. as 51 psig (444 kPa).

The autoclave was then set to heat to 120° C. Within 25 minutes the temperature reached 120° C. at 280 psig (2015 kPa). The temperature was held at 120° C. for 2.2 h; during this time, the pressure climbed to about 405 psig (2917 kPa).

A sample of the reactor vapor at this point had the following composition:

| Component | GC Area % |
|---|---|
| CF$_3$CH=CHF | 1.1 |
| CF$_3$CH$_2$CHF$_2$ | 3.1 |
| CF$_3$CH=CHCl | 91.1 |
| CF$_3$CH$_2$CHClF | 3.1 |
| C$_3$H$_2$ClF$_3$ isomer | 2.0 |
| C$_3$H$_3$Cl$_2$F$_3$ isomer | 0.1 |
| Unknowns (2) | 1.1 |

What is claimed is:

1. A process for producing a compound of the formula CF$_3$CHXCF$_{3-z}$Y$_z$, wherein X and Y are independently selected from the group consisting of H and Cl and z is 0 or 1, comprising:

(1) contacting starting material selected from the group consisting of a compound of the formula $CCl_3CHXCCl_{3-z}Y_z$, and mixtures thereof, with hydrogen fluoride at a temperature of less than 200° C. to produce a fluorination produce of said starting material which includes at least 90 mole percent of compounds selected from the group consisting of saturated compounds having the formula $C_3HXY_zCl_{6-z-x}F_x$ and olefinic compounds of the formula $C_3XY_zCl_{5-z-y}F_y$, wherein x is an integer from 1 to 6-z and y is an integer from 1 to 5-z, said fluorination product including no more than about 40 mole percent $CF_3CHXCF_{3-z}Y_z$;

(2) contacting compounds selected from the group consisting of said saturated compounds and said olefinic compounds produced in (1) with hydrogen fluoride in the vapor phase at a temperature of from 200° C. to about 400° C. in the presence of a fluorination catalyst; and (3) reacting a sufficient amount of said saturated compounds, wherein x is an integer from 1 to 5-z and said olefinic compounds produced in (1) with hydrogen fluoride in the vapor phase at a temperature of from 200° C. to about 400° C. in the presence of a vapor phase fluorination catalyst to provide an overall selectivity to $CF_3CHXCF_{3-z}Y_z$ of at least about 90 percent based upon the amount of starting material reacted with HF in (1) and (2).

2. The process of claim 1 wherein $CF_3CH_2CF_3$ is produced from $CCl_3CH_2CCl_3$ starting material.

3. The process of claim 2 wherein the vapor phase fluorination catalyst of (2) and (3) is a catalyst comprising trivalent chromium.

4. The process of claim 3 wherein the vapor phase fluorination catalyst is selected from the group consisting of catalysts prepared by pyrolysis of $(NH_4)_2Cr_2O_7$ to produce $Cr_2O_3$ and pretreatment with HF and catalysts prepared by pretreating $Cr_2O_3$ having a surface area greater than about 200 m²/g with HF.

5. The process of claim 4 wherein a sufficient amount of said saturated compounds wherein x is from 1 to 5 and said olefinic compounds are reacted to provide an overall selectivity to $CF_3CH_2CF_3$ of at least about 95 percent based upon the amount of $CCl_3CH_2CCl_3$ reacted with HF.

6. The process of claim 2 wherein in (1) $CCl_3CH_2CCl_3$ is reacted with HF in the liquid phase in a first reaction zone; wherein compounds selected from the group consisting of saturated compounds having the formula $C_3H_2F_xCl_{6-x}$ and olefinic compounds having the formula $C_3HF_yCl_{5-y}$ are vaporized from said first reaction zone at a temperature less than 200° C. and fed to a second reaction zone; and wherein the contact of (2) is in said second reaction zone.

7. The process of claim 2 wherein in (1) $CCl_3CH_2CCl_3$ is reacted with HF in the liquid phase in the presence of a liquid phase fluorination catalyst selected from the group consisting of carbon, $AlF_3$, $BF_3$ and $FeZ_3$ supported on carbon, where Z is selected from the group consisting of Cl and F, $SbCl_{3-a}F_a$ where a is from 0 to 3, $AsF_3$, $MCl_{5-b}F_b$ where M is selected from the group consisting of Sb, Nb, Ta and Mo, and b is from 0 to 5, and $M'Cl_{4-c}F_c$ where M' is selected from the group consisting of Sn, Ti, Zr and Hf, and c is from 0 to 4.

8. The process of claim 2 wherein (1) is carried out in a first reaction zone and (2) is carried out in a second reaction zone; and wherein essentially the entire effluent from the first reaction zone is fed to the second reaction zone.

9. The process of claim 2 wherein (1) is carried out in a first reaction zone and (2) is carried out in a second reaction zone; and wherein compounds selected from the group consisting of saturated compounds of the formula $C_3H_2F_xCl_{6-x}$ and olefinic compounds of the formula $C_3HF_yCl_{5-y}$ in the effluent from the second reaction zone are recycled to the first reaction zone, to the second reaction zone, or to both the first and second reaction zones.

10. The process of claim 2 wherein $CCl_2=CHCF_3$ is produced in (1) and reacted in (3).

11. The process of claim 2 wherein a catalyst is not present in (1).

* * * * *